United States Patent [19]

Dao-Cong et al.

[11] Patent Number: 5,550,280

[45] Date of Patent: Aug. 27, 1996

[54] HINDERED AROMATIC ESTER COMPOUNDS USEFUL AS ANTI-VIRAL AGENTS

[75] Inventors: Dong Dao-Cong; William A. Harrison, both of Guelph, Canada

[73] Assignee: Uniroyal Chemical Ltd./ Uniroyal Chemical Ltee, Elmira, Canada

[21] Appl. No.: 346,811

[22] Filed: Nov. 30, 1994

[51] Int. Cl.$^6$ .................. C07C 255/49; C07D 291/04; C07D 327/06

[52] U.S. Cl. .................. 558/415; 548/122; 548/127; 548/128; 548/131; 548/134; 548/136; 548/143; 548/146; 548/206; 548/236; 548/248; 548/334.1; 548/374.1; 548/491; 548/530; 549/14; 549/72; 549/356; 549/378; 549/429

[58] Field of Search .................. 549/29, 429, 14, 549/429, 378, 72, 356; 558/415; 548/146, 236, 248, 206, 127, 128, 134, 136, 374.1, 530, 334.1, 122, 131, 143, 491

[56] References Cited

U.S. PATENT DOCUMENTS 5,268,389  12/1993  Harrison .................. 514/485

FOREIGN PATENT DOCUMENTS 0104070  3/1984  European Pat. Off. .

*Primary Examiner*—Joseph Conrad
*Attorney, Agent, or Firm*—Daniel Reitenbach

[57] ABSTRACT

Compounds of the formula

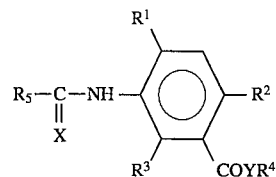

wherein
X is O or S;
Y is O or S;
$R^1$ is hydrogen, halogen, $C_1$–$C_4$ alkyl or $C_1$–$C_4$ alkoxy;
$R^2$ is hydrogen, halogen, $C_1$–$C_4$ alkyl, $C_1$–$C_4$ alkoxy, $C_2$–$C_4$ alkenyl, $C_2$–$C_4$ alkenyloxy, $C_2$–$C_4$ alkynyl, $C_2$–$C_4$ alkynyloxy, mono-, di- or tri-halomethyl, trifluoromethoxy, $C_1$–$C_4$ alkylthio, $C_3$–$C_4$ branched alkylthio, nitro, or cyano;
$R^3$ is hydrogen, halogen, methyl, mono-, di- or tri-halomethyl;
$R^4$ is
  a) $C_3$–$C_8$ cycloalkyl substituted by one or more $C_1$–$C_4$ alkyl, preferably one or two methyl;
or
  b)

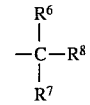

wherein
$R^6$ and $R^7$ are independently, hydrogen or linear or branched, $C_1$–$C_4$ alkyl, $C_2$–$C_4$ alkenyl, or $C_2$–$C_4$ alkynyl, and $R^8$ is $C_3$–$C_8$ cycloalkyl substituted by one or more $C_1$–$C_4$ alkyl; and
$R^5$ is an acyclic or cyclic side chain as defined herein.

These compounds are useful for inhibiting the growth or replication of retroviruses such as HIV.

3 Claims, No Drawings

HINDERED AROMATIC ESTER COMPOUNDS USEFUL AS ANTI-VIRAL AGENTS

FIELD OF THE INVENTION

This invention relates to novel hindered aromatic ester compounds. In particular, this invention relates to novel hindered aromatic ester compounds useful as anti-viral agents. More particularly, this invention relates to novel hindered aromatic ester compounds useful as agents against certain retroviruses such as the members of the group of Human Immunodeficiency Viruses (HIV).

BACKGROUND OF THE INVENTION

Retroviruses are viruses whose replication requires the transcription of viral RNA into DNA using the viral reverse transcriptase molecules attached to the viral RNA. This reverse transcription is the opposite of normal transcription which makes RNA from DNA.

Known retroviruses include HIV-1, HIV-2, the herpes family of viruses, HTLV-1 and cytomegalovirus (CMV). HIV, the virus which is presently believed to cause acquired immunodefiency syndrome (AIDS), is considered one of the principle threats to human life and health worldwide.

Various anti-HIV compounds have been proposed as useful in the treatment and prevention of AIDS, e.g., zidovudine (AZT), didanosine (ddI), zalcitabine (ddC), nevirapine, and dextran sulfate. However, none of the proposed compounds have been proven to be totally effective in the treatment or prevention of AIDS. For example, the three currently FDA approved compounds for the treatment of AIDS, i.e., AZT, ddI and ddC, can all cause undesirable side effects in a patient, such as inhibition of bone marrow cell growth, and their effectiveness is limited by virus mutation.

U.S. Pat. No. 5,268,389 describes certain thoicarboxylate ester compounds useful for inhibiting the growth or replication of HIV.

It is the purpose of this invention to provide novel hindered aromatic ester compounds useful as anti-viral agents which are less susceptible to plasma or liver esterases and which have low total body clearance.

It is also the purpose of this invention to provide a method for inhibiting or preventing the growth or replication of human immunodeficiency viruses using the novel hindered aromatic ester compounds.

Finally, it is also the purpose of this invention to provide compositions useful for inhibiting or preventing the growth or replication of human immunodeficiency viruses, comprising the novel hindered aromatic ester compounds.

DESCRIPTION OF THE INVENTION

This invention relates to a compound of the formula

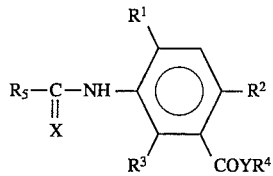

wherein

X is O or S, preferably S;

Y is O or S, preferably O;

$R^2$ is hydrogen, halogen, $C_1$–$C_4$ alkyl or $C_2$–$C_4$ alkoxy;

$R^2$ is hydrogen, halogen, $C_1$–$C_4$ alkyl, $C_1$–$C_4$ alkoxy, $C_2$–$C_4$ alkenyl, $C_2$–$C_4$ alkenyloxy, $C_2$–$C_4$ alkynyl, $C_2$–$C_4$ alkynyloxy, mono-, di- or tri-halomethyl, trifluoromethoxy, $C_1$–$C_4$ alkylthio, $C_3$–$C_4$ branched alkylthio, nitro, or cyano;

$R^3$ is hydrogen, halogen, methyl, mono-, di- or tri-halomethyl;

$R^4$ is
a) $C_3$–$C_8$ cycloalkyl substituted by one or more $C_1$–$C_4$ alkyl, preferably one or two methyl;
or
b)

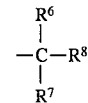

wherein $R^6$ and $R^7$ are independently, hydrogen or linear or branched, $C_1$–$C_4$ alkyl, $C_2$–$C_4$ alkenyl, or $C_2$–$C_4$ alkynyl, and $R^8$ is $C_3$–$C_8$ cycloalkyl substituted by one or more $C_1$–$C_4$ alkyl, preferably one or two methyl; and $R^5$ is
a) fully unsaturated, partially or fully reduced or substituted oxathiinyl, furanyl, dithiinyl, dioxinyl, thienyl, thiazolyl, oxazolyl, isoxazolyl, isothiazolyl, thiadiazolyl, pyrazolyl, pyrrolyl, imidazolyl, pyranyl, oxathiazinyl, oxadiazolyl, dihydrofuranyl, dihydro-2-dioxinyl or indolyl;

b) substituted or unsubstituted, linear or branched $C_1$–$C_8$ alkyl, $C_2$–$C_8$ alkenyl, $C_2$–$C_8$ alkynyl or $C_1$–$C_8$ mono- or di-alkylamino; $C_3$–$C_7$ cycloalkyl, $C_3$–$C_7$ cycloalkylalkoxy, cycloalkenyl, unsubstituted or substituted by $C_1$–$C_6$ alkyl; $C_7$–$C_{10}$ phenylalkyl, $C_1$–$C_8$ alkoxy, $C_1$–$C_8$ alkoxycarbonyl, $C_2$–$C_8$ mono-, di- or tri-haloalkoxy, $C_2$–$C_8$ alkenyloxy, or $C_2$–$C_8$ alkynyloxy;

c) aryl, aralkyl, aryloxyalkyl, or cycloalkylaryloxy, wherein the alkyl moiety is $C_1$–$C_4$, the cycloalkyl moiety is $C_3$–$C_8$, and the aryl moiety is naphthyl, phenyl, or phenyl substituted by one or more halogen, carboxy, $C_1$–$C_8$ alkyl, $C_1$–$C_8$ haloalkyl, $C_1$–$C_8$ alkylthio, phenyl, nitro, amino, $C_1$–$C_8$ alkoxycarbonylamino, hydroxyl, acetyl, acetyloxy, phenoxy, or $C_1$–$C_8$ alkylcarbonyl;

or d) G—O— wherein G is a linear or branched, unsubstituted or halo-substituted, $C_1$–$C_8$ alkyl, $C_2$–$C_8$ alkenyl, or $C_2$–$C_8$ alkynyl; a $C_3$–$C_7$ cycloalkyl or cycloalkenyl, unsubstituted or substituted by $C_1$–$C_6$ alkyl; a phenyl or phenyl substituted by halogen, $C_1$–$C_8$ alkyl, $C_1$–$C_6$ alkoxy, carboxyl, $C_1$–$C_8$ alkylthio, phenyl, nitro, amino, hydroxyl, acetyl, acetyloxy, phenoxy, $C_1$–$C_8$ alkoxycarbonyl, $C_2$–$C_8$ alkoxycarbonyl furanylalkyl, tetrahydrofuranylalkyl, oxetanylalkyl or oxiranylalkyl.

Preferably, $R^4$ is 2,6-dimethylcyclohexyl, 2,5-dimethylcyclopentyl, 2,4-dimethylcyclobutyl, 2,3-dimethylcyclopropyl, 1-, 2- or 3-methylcyclopentyl, 1- or methylcyclohexyl, 1-methylcyclobutyl, 1-methylcyclopropyl, or dicyclopropyl;

More preferably, $R^1$ is hydrogen, $R^2$ is halogen, $R^3$ is hydrogen, $R^4$ is 1-, 2- or 3-methylcyclopentyl, or 2,6-dimethylcyclohexyl, and $R^5$ is phenyl, halophenyl, phenylamino, phenylalkylamino, tolyl, phenylmethoxy, or furanyl, thiophenyl, pyrrolyl, N-methyl pyrrolyl, or oxathiinyl, unsubstituted or substituted by $C_1-C_3$ alkyl.

Also preferred are those compounds of formula I wherein $R^1$ is hydrogen, $R^m$ is halogen, $R^3$ is hydrogen, $R^4$ is 1-, 2-, or 3-methylcyclopentyl or 2,6-dimethylcyclohexane, and $R^5$ is linear or branched $C_3-C_6$ alkyl, $C_2-C_6$ alkenyl or alkynyl, $C_1-C_8$ alkoxy, $C_2-C_8$ alkenyloxy, or $C_2-C_8$ alkynyloxy; $C_3-C_7$ cycloalkyl or $C_3-C_7$ cycloalkenyl unsubstituted or substituted by $C_1-C_6$ alkyl; or $C_3-C_8$ cycloalkyloxy.

Particularly preferred are those compounds of formula I wherein X is S, Y is O, $R^1$ is hydrogen, $R^2$ is chloro, $R^3$ is hydrogen, and $R^5$ is phenyl, 2-fluorophenyl, 2-methyl-3-furanyl or 5,6-dihydro-2-methyl-1,4-oxathiin-3-yl.

The compounds of this invention are useful for the inhibition of the growth or replication of retroviruses, particularly human immunodeficiency viruses such HIV-1, in vitro and in vivo. The compounds are useful in the therapeutic or prophylactic treatment of diseases caused by retroviruses, such as acquired immune deficiency syndrome or an HIV infection in a human or other mammal.

It is intended that the scope of this invention encompass all isomers, including positional or stereoisomers, of any compound of formula I exhibiting isomerism. It is also intended that any novel processes or intermediates for synthesizing said compounds be included within the scope of this invention.

METHOD OF SYNTHESIS

The compound of formula I in which X is O and $R^5$ is oxathienyl, furanyl, thienyl, pyrrolyl, other heterocyclyl, or substituted phenyl, may be prepared from the appropriate carboxylic acid ($R^5COOH$) or acid chloride ($R^5COCl$), and an aniline derivative of the formula

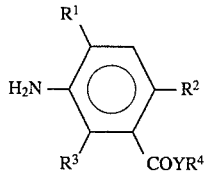

by using one of the conventional methods of amide bond formation. The amide bond formation reaction is conducted in an appropriate solvent, such as methylene chlorde toluene, methyl ethyl ketone, tetrahydrofuran, dimethylformamide or acetonitrile, at a temperature of about 0° C. to about 100° C. It is usually preferable to conduct the reaction in the presence of a base, such as triethylamine or pyridine. Other reactive derivatives of the carboxylic acid can be employed. For example, the anhydride of the carboxylic acid or a mixed anhydride, such as alkoxycarbonyloxy derivative, can be reacted with aniline derivative. Alternatively, the carboxylic acid and aniline derivative can be reacted directly in the presence of a condensing agent such as dicyclohexyl-carbodiimide to form the amide.

The aniline derivative can be prepared by reduction of the corresponding nitro compound by methods known in the art, for example, with hydrogen and a catalyst, such as Raney nickel or platinum, or with a metal-acid combination, such as iron or tin, and hydrochloric acid or acetic acid.

Other compounds of formula I wherein $R^5$ is an alkoxy can be prepared by reacting the appropriate aniline derivative with an alkoxycarbonyl chloride, under conditions essentially similar to those used for reaction of an acid chloride with the aniline derivative. They can also be prepared by reacting the appropriate isocyanate derivative with an alcohol. The isocyanate can be prepared by reacting the aniline derivative or a suitable salt thereof, such the hydrochloride, with phosgene or a phosgene substitute, such trichloromethyl chloroformate.

The compounds of formula I wherein $R^5$ is alkoxy and X is sulphur can be similarly prepared using alkoxy thiocarbonylchloride under conditions described above, or from the appropriate isothiocyanate derivative and an alcohol.

Thiocarboxanilides of formula I wherein X is S and $R^5$ is furanyl, thienyl, pyrrolyl, other heterocyclyl, or substituted phenyl, can be prepared by reacting the corresponding amide with sulfurating agent such as Lawesson's Reagent or phosphorus pentasulfide in a suitable solvent such as toluene, xylene, DME, pyridine, etc.

Syntheses using Lawesson's Reagent are described in *Advanced Organic Chemistry*, J. March, pp. 893–894 (John Wiley & Sons, New York, 1992). Methods using phosphorus pentasulfide are described in *Reagents for Organic Synthesis*, Volume 1, Fieser & Fieser, pp. 870–871 (John Wiley & Son, New York, 1967).

The following examples are provided to illustrate the methods for synthesizing compounds of this invention.

EXAMPLES

These examples illustrate the synthesis of the compounds of this invention by the following general reaction scheme:

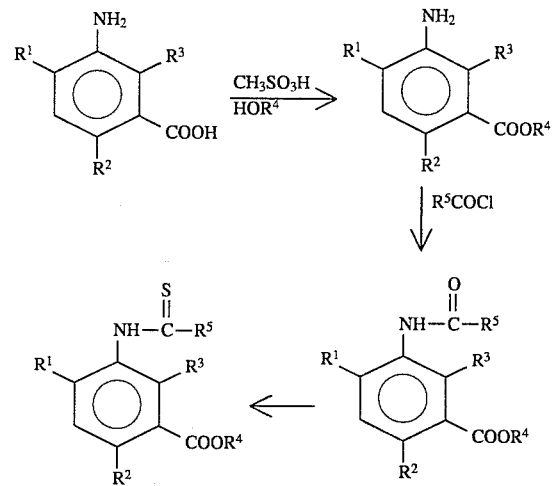

A. Preparation of 2-methylcyclohexyl 5-amino-2-chlorobenzoate

Methanesulfonic acid (99%, 100 g, 1.0 mole) was added slowly to a stirred mixture of 5-amino-2-chlorobenzoic acid (85%, 100 g, 0.5 mole) in 2-methylcyclohexanol (200 g, 1.85 mole). The mixture was heated under reflux with stirring for 6 hours, then the excess 2-methylcyclohexanol was evaporated under reduced pressure. The residue was then dissolved in methylene chloride (800 ml), washed with water (300 ml), 5% sodium bicarbonate solution (300 ml), water (300 ml), dried (magnesium sulfate), and filtered. The solvent was then evaporated to give 109 g of 2-methylcyclohexyl 5-amino-2-chlorobenzoate as a light brown oil.

NMR spectrum ($CDCl_3$) gave ppm values: 0.9–2.0 (12H, m), 3.5 (2H, s), 4.75 (1H, m), 6.5–7.4 (3H, m).

B. Preparation of 2-methylcyclohexyl 2-chloro-5 (benzoylamino) benzoate (Compound 9)

Benzoyl chloride (5.2 g, 0.037 mole) was added slowly at room temperature to a stirred mixture of 2-methylcyclohexyl 5-amino-2-chlorobenzoate (10 g, 0.037 mole), triethylamine (4.0 g, 0.04 mole) dissolved in methylene chloride (100 ml). This reaction mixture was stirred at room temperature for 20 hours. The reaction mixture was then washed with water (200 ml), 3% HCl solution (100 ml), 2% NaOH solution (100 ml) and water (100 ml), dried (magnesium sulfate) and filtered. The solvent was evaporated off to give a brown oil which was crystallized with ethyl/hexane to give 2-methylcyclohexyl 2-chloro-5-(benzoylamino)benzoate as a white solid (5 g, m.p. 121°–122° C.)

NMR spectrum (CDCl$_3$) gave ppm values: 0.8–2.2 (12H, m), 4.65 (1H, m), 7.2–7.55 (4H, m), 7.7–8.2 (4H, m), 8.85 (1H, bs).

C. Preparation of 2-methylcyclohexyl 2-chloro-5-[(phenylthioxomethyl)amino] benzoate (Compound 5)

To a solution of 2-methylcyclohexyl 2-chloro-5-(benzoylamino)benzoate (1.8 g, 0.0048 mole) in toluene (100 ml) was added Lawesson's Reagent (2.5 g), sodium bicarbonate (1.0 g) to produce the reaction mixture. The reaction mixture was stirred and refluxed for 4 hours. The reaction mixture was then cooled to ambient temperature which resulted in the formation of a white solid precipitate. The white solid was filtered off. The filtrate was then passed through a short column of aluminum oxide (neutral) using ether/hexane as eluent to give a yellow solution. The yellow solution was concentrated and a yellow solid crystallized. The yellow solid was filtered to give 2-methylcyclohexyl 2-chloro-5-[(phenylthioxomethyl)amino] benzoate as a yellow solid (1.3 g, m.p. 143°–144° C.).

NMR spectrum (CDCl$_3$) gave ppm values: 0.8–2.2 (12H, m), 4.7(1H, m), 7.2–8.2 (8H, m), 9.7 (1H, bs).

Table I below lists representative compounds of this invention.

In the test assay, small amounts of HIV are added to T4 lymphocyte cells. The assay measures the amount of T4 lymphocytes "killed" by HIV cytolysis. Since a complete cycle of viral reproduction is necessary to "kill" the T4 lymphocyte cells, agents that interfere with viral reproduction will protect the cells from cytolysis.

The NCI system is automated in several features to accomodate large numbers of candidate agents and is generally designed to detect anti-HIV activity. Compounds that degenerate or are rapidly metabolized in the culture conditions do not show activity in this screen. All tests are compared with at least one positive (AZT-treated) control done at the same time under identical conditions.

The Test Procedure

1) The test compound was dissolved in dimethyl sulfoxide and diluted 1:100 in cell culture medium before serial half-log$_{10}$ dilutions were prepared. T4 lymphocytes (CEM cell line) were then added to the cell culture medium, and, finally, after a brief interval, HIV-1 was added, resulting in a 1:200 final dilution of the test compound. Uninfected cells in the cell culture medium containing the test compound (i.e., minus HIV-1) were used as a toxicity control, and infected cells in the cell culture medium without the test compound and uninfected cells in the cell culture medium without the test compound, were used as basic controls.

2) The cultures were incubated at 37° C. in a 5% carbon dioxide atmosphere for 6 days.

3) The tetrazolium salt, XTT, was added to all wells, and the cultures were then incubated to allow formazan color development by viable cells.

4) Individual wells were analyzed spectrophotometrically to quantitate formazan production, and were also viewed microscopically for detection of viable cells and confirmation of protective activity.

TABLE I

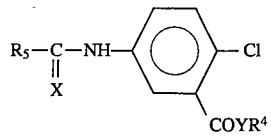

| CMPD # | R$^5$ | X | Y | R$^4$ | mp (°C.) |
|---|---|---|---|---|---|
| 1 | Phenyl | O | O | 1-methylcyclopentyl | 111–112 |
| 2 | Phenyl | S | O | 1-methylcyclopentyl | 94–96 |
| 3 | Phenyl | S | O | 2-methylcyclopentyl | 80–81 |
| 4 | Phenyl | S | O | 2,6-dimethylcyclohexyl | 142–143 |
| 5 | Phenyl | S | O | 2-methylcyclohexyl | 143–144 |
| 6 | 5,6-dihydro-2-methyl-1,4-oxathiin-3-yl | O | O | 2-methylcyclohexyl | 93–95 |
| 7 | Phenyl | O | O | 3-methylcyclopentyl | 73–75 |
| 8 | Phenyl | S | O | 3-methylcyclopentyl | syrup |
| 9 | Phenyl | O | O | 2-methylcyclohexyl | 121–122 |
| 10 | 2-CH$_3$-Phenyl | O | O | 2-methylcyclohexyl | 82–84 |
| 11 | 2-CH$_3$-Phenyl | S | O | 2-methylcyclohexyl | syrup |
| 12 | Phenyl | S | O | 1-cyclopentylethyl | syrup |
| 13 | Phenyl | S | O | 1-cyclopropylethyl | syrup |
| 14 | 2-CH$_3$-3-Furanyl | O | O | 1-cyclopentylethyl | 91–92 |
| 15 | 2-CH$_3$-3-Furanyl | O | O | 1-cyclopropylethyl | 113–114 |
| 16 | 2-CH$_3$-3-Furanyl | S | O | 1-cyclopropylethyl | syrup |
| 17 | N-CH$_3$-2-Pyrrolyl | O | O | 1-cyclopropylethyl | 134–135 |

VITRO SCREENING RESULTS

Representative compounds of this invention were tested for anti-viral activity by subjecting them to standard National Cancer Institute ("NCI") in vitro screening procedures. Two blanks were run with each test. The NCI test for agents active against HIV is designed to detect agents acting at any stage of the virus reproduction cycle.

5) Virus-infected cells exposed to the test compound were compared with noninfected cells exposed to the test compound, and with other appropriate controls (infected cells not exposed to the test compound and noninfected cells not exposed to the test compound, wells containing only the test compound in the cell culture medium, and so on) on the same plate. These are the first and second blanks described below.

6) Data were reviewed in comparison with other tests done at the same time and a determination concerning activity was made. In the first blank, HIV and T4 lymphocytes in cell culture medium, were incubated together to measure the infectivity of the virus. The viability of the cells was measured after holding for six or seven days. In an "effective" test, most cells were infected before the holding period was complete.

In the second blank, the T4 lymphocytes in cell culture medium and the test compound (with no HIV-1) were incubated together to measure the toxicity of the drug to the cellline. The viability of the cells was measured as a function of concentration of the compound, after incubation for seven days. The concentration of the test compound that results in 50% inhibition of cell growth is defined as its $IC_{50}$.

Finally, the protective effects of the test compounds were measured. Each cell culture and test compound were incubated with the virus and the viability of the cells was measured as a function of compound concentration after incubation for six or seven days. The concentration of the test compound that results in 50% "control," i.e., a 50% reduction of the viral cytopathic effect, is defined as its $EC_{50}$. The therapeutic index $TI_{50}$ was calculated as $IC_{50}/EC_{50}$.

Concentrations of test compounds required for between 20 and 50% reduction of the viral cytopathic effect can also be determined. Such compounds are classified as moderately active. Compounds with less than 20% control are considered inactive.

The compounds were tested to determine their reduction of HIV cytopathic effect on the human cell line CEM. Tests were done by innoculating these cell lines in-well (IW), i.e., the test compound and CEM cells were mixed on a test plate and the virus was added a short time later.

TABLE 2

| Compound | $IC_{50}$ (M) | $EC_{50}$ (M) | $TI_{50}$ |
|---|---|---|---|
| 1 | $4.18 \times 10^{-5}$ | $1.73 \times 10^{-5}$ | 2 |
|   | $4.95 \times 10^{-5}$ | $1.15 \times 10^{-5}$ | 4 |
|   | $3.27 \times 10^{-5}$ | $1.52 \times 10^{-5}$ | 2 |
|   | $3.20 \times 10^{-5}$ | $1.76 \times 10^{-5}$ | 2 |
| 2 | $2.94 \times 10^{-5}$ | $2.16 \times 10^{-7}$ | 137 |
|   | $2.88 \times 10^{-5}$ | $2.32 \times 10^{-7}$ | 124 |
|   | $3.10 \times 10^{-5}$ | $3.98 \times 10^{-7}$ | 78 |
|   | $3.20 \times 10^{-5}$ | $5.98 \times 10^{-7}$ | 54 |
| 3 | $1.41 \times 10^{-5}$ | $9.67 \times 10^{-8}$ | 146 |
|   | $1.22 \times 10^{-5}$ | $8.67 \times 10^{-8}$ | 141 |
|   | $1.41 \times 10^{-5}$ | $7.83 \times 10^{-8}$ | 180 |
|   | $1.38 \times 10^{-5}$ | $1.01 \times 10^{-7}$ | 136 |
| 4 | $>1.30 \times 10^{-5}$ | $9.40 \times 10^{-7}$ | >14 |
|   | $>1.30 \times 10^{-5}$ | $2.10 \times 10^{-6}$ | >6 |
|   | $>1.30 \times 10^{-5}$ | $9.50 \times 10^{-7}$ | >14 |
|   | $>1.30 \times 10^{-5}$ | $3.70 \times 10^{-7}$ | >35 |
| 5 | $1.60 \times 10^{-5}$ | $1.75 \times 10^{-7}$ | 92 |
|   | $1.41 \times 10^{-5}$ | $1.99 \times 10^{-7}$ | 71 |
|   | $1.36 \times 10^{-5}$ | $7.91 \times 10^{-8}$ | 172 |
|   | $1.34 \times 10^{-5}$ | $1.26 \times 10^{-7}$ | 107 |
| 6 | $>2.40 \times 10^{-5}$ | $2.20 \times 10^{-5}$ | >1 |
|   | $>2.40 \times 10^{-5}$ | $1.40 \times 10^{-6}$ | >18 |
|   | $1.40 \times 10^{-5}$ | $7.30 \times 10^{-7}$ | 19 |
|   | $2.00 \times 10^{-5}$ | $1.10 \times 10^{-6}$ | 18 |
| 7 | $1.90 \times 10^{-5}$ | $5.70 \times 10^{-6}$ | 3 |
|   | $1.10 \times 10^{-5}$ | $5.80 \times 10^{-6}$ | 2 |
|   | $1.70 \times 10^{-5}$ | $3.60 \times 10^{-6}$ | 5 |
|   | $1.40 \times 10^{-5}$ | $6.10 \times 10^{-6}$ | 2 |
| 8 | $1.46 \times 10^{-5}$ | $2.13 \times 10^{-7}$ | 68 |
|   | $1.35 \times 10^{-5}$ | $1.95 \times 10^{-7}$ | 69 |
|   | $1.48 \times 10^{-5}$ | $1.84 \times 10^{-7}$ | 80 |
|   | $1.31 \times 10^{-5}$ | $1.81 \times 10^{-7}$ | 72 |
| 9 | $1.42 \times 10^{-5}$ | $4.65 \times 10^{-6}$ | 31 |

TABLE 2-continued

| Compound | $IC_{50}$ (M) | $EC_{50}$ (M) | $TI_{50}$ |
|---|---|---|---|
|   | $1.26 \times 10^{-5}$ | $4.47 \times 10^{-6}$ | 28 |
|   | $1.53 \times 10^{-5}$ | $2.37 \times 10^{-6}$ | 65 |
|   | $1.45 \times 10^{-5}$ | — | — |
| 10 | $1.97 \times 10^{-5}$ | $2.39 \times 10^{-6}$ | 8 |
|   | $1.69 \times 10^{-5}$ | $1.75 \times 10^{-6}$ | 10 |
|   | $1.71 \times 10^{-5}$ | $1.30 \times 10^{-6}$ | 13 |
|   | $1.66 \times 10^{-5}$ | $1.13 \times 10^{-6}$ | 15 |
| 11 | $>9.40 \times 10^{-6}$ | $5.00 \times 10^{-6}$ | >2 |
|   | $>9.40 \times 10^{-6}$ | $5.40 \times 10^{-6}$ | >2 |
|   | $>9.40 \times 10^{-6}$ | $5.40 \times 10^{-6}$ | >2 |
|   | $>9.40 \times 10^{-6}$ | $5.00 \times 10^{-6}$ | >2 |
|   | $>9.40 \times 10^{-6}$ | $5.40 \times 10^{-6}$ | >2 |
|   | $>9.40 \times 10^{-6}$ | $4.40 \times 10^{-6}$ | >2 |
| 12 | $>1.4 \times 10^{-5}$ | $2.8 \times 10^{-7}$ | >48 |
|   | $>1.4 \times 10^{-5}$ | $2.3 \times 10^{-7}$ | >60 |
|   | $>1.4 \times 10^{-5}$ | $2.7 \times 10^{-7}$ | >50 |
| 13 | $>3.8 \times 10^{-5}$ | $2.1 \times 10^{-6}$ | >18 |
|   | $>3.8 \times 10^{-5}$ | $2.2 \times 10^{-6}$ | >17 |
|   | $>3.8 \times 10^{-5}$ | $7.9 \times 10^{-7}$ | >48 |
|   | $>3.8 \times 10^{-5}$ | $7.2 \times 10^{-7}$ | >52 |
| 14 | $7.7 \times 10^{-6}$ | $8.4 \times 10^{-7}$ | 9 |
|   | $>1.4 \times 10^{-5}$ | $1.1 \times 10^{-6}$ | >13 |
|   | $>1.4 \times 10^{-5}$ | $7.7 \times 10^{-7}$ | >18 |
|   | $>1.4 \times 10^{-5}$ | $2.3 \times 10^{-6}$ | >6 |
|   | $>1.4 \times 10^{-5}$ | $1.7 \times 10^{-6}$ | >8 |
| 15 | $>2.1 \times 10^{-5}$ | $1.4 \times 10^{-6}$ | >14 |
|   | $>2.1 \times 10^{-5}$ | $2.5 \times 10^{-6}$ | >8 |
|   | $>2.1 \times 10^{-5}$ | $1.1 \times 10^{-6}$ | >19 |
| 16 | $>2.0 \times 10^{-5}$ | $<6.3 \times 10^{-9}$ | — |
|   | $>2.0 \times 10^{-5}$ | $4.5 \times 10^{-8}$ | >440 |
|   | $>2.0 \times 10^{-5}$ | $8.2 \times 10^{-8}$ | >240 |
|   | $>2.0 \times 10^{-5}$ | $1.3 \times 10^{-8}$ | >1600 |
| 17 | $>5.4 \times 10^{-5}$ | $5.3 \times 10^{-6}$ | >10 |
|   | $>5.4 \times 10^{-5}$ | $9.7 \times 10^{-6}$ | >6 |
|   | $>5.4 \times 10^{-5}$ | $5.0 \times 10^{-6}$ | >11 |
|   | $>5.4 \times 10^{-5}$ | $4.1 \times 10^{-6}$ | >13 |

The compounds of this invention can be used in the form of salts derived from inorganic or organic acids. Examples of acids which may be employed to form pharmaceutically acceptable acid salts include such inorganic acids as hydrochloric acid, sulphuric acid and phosphoric acid, and such organic acids as oxalic acid, maleic acid, succinic acid and citric acid.

The compounds of the present invention can be administered orally, parenterally, sublingually, by inhalation spray, rectally, or topically in dosage unit formulations containing conventional non-toxic pharmaceutically acceptable carriers, adjuvants, and vehicles. Suitable carrier, adjuvants and vehicles can be found in standard pharmaceutical texts such as, *Remington's Pharmaceutical Sciences*, 16th Edition, Mack Publishing Company, Easton, Pa. (1980).

The amount of the compound of this invention that can be combined with the carrier to produce a single dosage form will vary depending upon the host treated, the particular disease to be treated, and the particular mode of administration. In general, the compound of this invention is most desirably administered at a concentration level that will generally afford anti-virally effective results without causing any harmful or deleterious side effects.

While the compounds of this invention can be administered as sole active pharmaceutical agents, each compound can also be used in combination with one or more immunodulators, antiviral agents, or other anti-infective agents or vaccines, such as AZT, nevirapine, acylclovir, alpha or beta interferon, etc.

It will be understood that agents which can be combined with the compounds of this invention for the therapeutic or prophylactic treatment of AIDS or an HIV infection are not limited to those listed above, but include any agents useful for the therapeutic or prophylactic treatment of AIDS or an HIV infection which are not deleterious to the activity of the compounds of this invention or whose combination with the compounds of this invention will not have a deleterious effect on the host treated.

What is claimed is:

1. A compound of the formula

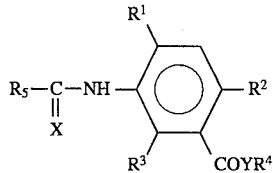

wherein

X is O or S;

Y is O or S;

$R^1$ is hydrogen, halogen, $C_1$–$C_4$ alkyl or $C_1$–$C_4$ alkoxy;

$R^2$ is hydrogen, halogen, $C_1$–$C_4$ alkyl, $C_1$–$C_4$ alkoxy, $C_2$–$C_4$ alkenyl, $C_2$–$C_4$ alkenyloxy, $C_2$–$C_4$ alkynyl, $C_2$–$C_4$ alkynyloxy, mono-, di- or tri-halomethyl, trifluoromethoxy, $C_1$–$C_4$ alkylthio, $C_3$–$C_4$ branched alkylthio, nitro, or cyano;

$R^3$ is hydrogen, halogen, methyl, mono-, di- or tri-halomethyl;

$R^4$ is a) $C_3$–$C_8$ cycloalkyl substituted by one or more $C_1$–$C_4$ alkyl;

or b)

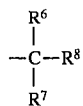

wherein $R^6$ and $R^7$ are independently, hydrogen or linear or branched, $C_1$–$C_4$ alkyl, $C_2$–$C_4$ alkenyl, or $C_2$–$C_4$ alkynyl, and $R^8$ is $C_3$–$C_8$ cycloalkyl substituted by one or more $C_1$–$C_4$ alkyl; and $R^5$ is a) fully unsaturated, partially or fully reduced or substituted oxathiinyl, furanyl, dithiinyl, dioxinyl, thienyl, thiazolyl, oxazolyl, isoxazolyl, isothiazolyl, thiadiazolyl, pyrazolyl, pyrrolyl, imidazolyl, pyranyl, oxathiazinyl, oxadiazolyl, dihydrofuranyl, dihydro-2-dioxinyl or indolyl; or b) G—O— wherein

G is a furanylalkyl, tetrahydrofuranylalkyl, oxetanylalkyl or oxiranylalkyl.

2. A compound of the formula

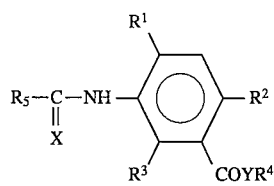

wherein

X is O or S;

Y is O or S;

$R^1$ is hydrogen, halogen, $C_1$–$C_4$ alkyl or $C_1$–$C_4$ alkoxy;

$R^2$ is hydrogen, halogen, $C_1$–$C_4$ alkyl, $C_1$–$C_4$ alkoxy, $C_2$–$C_4$ alkenyl, $C_2$–$C_4$ alkenyloxy, $C_2$–$C_4$ alkynyl, $C_2$–$C_4$ alkynyloxy, mono-, di- or tri-halomethyl, trifluoromethoxy, $C_1$–$C_4$ alkylthio, $C_3$–$C_4$ branched alkylthio, nitro, or cyano;

$R^3$ is hydrogen, halogen, methyl, mano-, di- or tri-halomethyl;

$R^4$ is a) 2,6-dimethylcyclohexyl, 2,5-dimethylcyclopentyl, 2,4-dimethylcyclobutyl, 2,3-dimethylcyclopropyl, 1-, 2- or 3-methylcyclopentyl, 1- or 2-methylcyclohexyl, 1-methylcyclobutyl, 1-methylcyclopropyl, or dicyclopropyl;

or b)

wherein $R^6$ and $R^7$ are independently hydrogen or $C_1$–$C_4$ alkyl and $R^8$ is 2,6-dimethylcyclohexyl, 2,5-dimethylcyclopentyl, 2,4-dimethylcyclobutyl, 2,3-dimethylcyclopropyl, 1-, 2- or 3-methylcyclopentyl, 1- or 2-methylcyclohexyl, 1-methylcyclobutyl, 1-methylcyclopropyl, or dicyclopropyl; and $R^5$ is a) fully unsaturated, partially or fully reduced or substituted oxathiinyl, furanyl, dithiinyl, dioxinyl, thienyl, thiazolyl, oxazolyl, isoxazolyl, isothiazolyl, thiadiazolyl, pyrazolyl, pyrrolyl, imidazolyl, pyranyl, oxathiazinyl, oxadiazolyl, dihydrofuranyl, dihydro-2-dioxinyl or indolyl; or b) G—O— wherein

G is a furanylalkyl, tetrahydrofuranylalkyl, oxetanylalkyl or oxiranylalkyl.

3. A compound as recited in claim 2 wherein $R^1$ is hydrogen, $R^2$ is halogen, $R^3$ is hydrogen, $R^4$ is 1-, 2- or 3-methylcyclopentyl, 2,5-dimethylcyclopentyl or 2,6-dimethylcyclohexyl, and $R^5$ is furan, thiophene, pyrrole, N-methyl pyrrole, or oxathiin, unsubstituted or substituted by $C_1$–$C_3$ alkyl.

* * * * *